(12) United States Patent
Kelley

(10) Patent No.: US 10,080,950 B2
(45) Date of Patent: Sep. 25, 2018

(54) SYSTEM OF COMMUNICATION IN A WEARABLE DEVICE

(71) Applicant: Aspire Sports Inc., Steubenville, OH (US)

(72) Inventor: Todd A Kelley, Steubenville, OH (US)

(73) Assignee: Aspire Sports Inc., Steubenville, OH (US)

( * ) Notice: Subject to any disclaimer, the term of this patent is extended or adjusted under 35 U.S.C. 154(b) by 254 days.

(21) Appl. No.: 14/846,742

(22) Filed: Sep. 5, 2015

(65) Prior Publication Data
US 2017/0065872 A1 Mar. 9, 2017

(51) Int. Cl.
| | | |
|---|---|---|
| *G06F 15/16* | (2006.01) | |
| *A63B 71/06* | (2006.01) | |
| *H04W 4/06* | (2009.01) | |
| *G06F 1/16* | (2006.01) | |
| *G06F 19/00* | (2018.01) | |
| *G09B 19/00* | (2006.01) | |
| *H01L 27/12* | (2006.01) | |

(Continued)

(52) U.S. Cl.
CPC .......... *A63B 71/0622* (2013.01); *G06F 1/163* (2013.01); *G06F 1/1652* (2013.01); *G06F 19/3481* (2013.01); *G09B 19/0038* (2013.01); *H01L 27/124* (2013.01); *H04W 4/06* (2013.01); *H04W 4/80* (2018.02); *A61B 5/681* (2013.01); *A61B 5/7435* (2013.01); *A61B 2503/10* (2013.01); *A63B 2071/0663* (2013.01); *A63F 2300/305* (2013.01)

(58) Field of Classification Search
CPC ........ A63B 71/0622; A63B 2071/0663; H01L 27/124; G06F 19/3481; G06F 1/1652; G06F 1/163; G09B 19/0038; H04W 4/008; H04W 4/06; H04L 12/189; A61B 5/7435; A61B 2503/10; A61B 5/681; A63F 2300/305
See application file for complete search history.

(56) References Cited

U.S. PATENT DOCUMENTS 8,764,212 B2 * 7/2014 Kim .................. G02F 1/133603
362/231
2010/0002418 A1 * 1/2010 Lin ...................... G02B 6/0085
362/97.1

(Continued)

*Primary Examiner* — Michael A Keller
(74) *Attorney, Agent, or Firm* — Jacob M. Ward; Ward Law Office LLC

(57) ABSTRACT

The present invention is directed to a system and method of distributing information and instructions for a wearable device, and for improving communication between players and coaches during a sporting event, more specifically allowing players to dynamically receive real-time communications from their coaches concerning game information and or instruction during the game. The wearable device incorporates a plastic flexible display screen for viewing information and instructions. These flexible displays screens are cited as being "unbreakable", because they are made completely of a thin conductive plastic substrates, and do not contain glass. Additionally, touch cell technology uses resistors to adjust the sensitivity of the detector cell which allows an actual touch to be detected on the flexible plastic display of the wearable device, which is designed to operate accurately and reliably in harsh environments.

5 Claims, 3 Drawing Sheets

(51) Int. Cl.
*H04W 4/80* (2018.01)
*A61B 5/00* (2006.01)

(56) References Cited

U.S. PATENT DOCUMENTS

| | | | | |
|---|---|---|---|---|
| 2010/0077536 A1* | 4/2010 | Daniel | ............... | A63B 71/0669 |
| | | | | 2/425 |
| 2010/0080388 A1* | 4/2010 | Daniel | ................... | A63B 71/06 |
| | | | | 380/270 |
| 2010/0080390 A1* | 4/2010 | Daniel | ................... | A63B 71/06 |
| | | | | 380/271 |
| 2012/0264549 A1* | 10/2012 | Homsi | ................ | A63B 43/008 |
| | | | | 473/422 |
| 2012/0327017 A1* | 12/2012 | Sekizawa | ................ | G06F 3/045 |
| | | | | 345/174 |
| 2013/0307809 A1* | 11/2013 | Sudou | ................... | G06F 3/0414 |
| | | | | 345/173 |
| 2014/0295918 A1* | 10/2014 | Grifoni | ............... | H04M 1/7253 |
| | | | | 455/566 |
| 2015/0110279 A1* | 4/2015 | Tejerina | ................... | G01H 3/14 |
| | | | | 381/56 |
| 2016/0158639 A1* | 6/2016 | Cantrell | ................ | A61B 5/681 |
| | | | | 340/815.4 |
| 2016/0202800 A1* | 7/2016 | Itaya | ....................... | G06F 3/044 |
| | | | | 345/174 |
| 2017/0086519 A1* | 3/2017 | Vigano' | ............. | A41D 19/0027 |
| 2017/0319430 A1* | 11/2017 | Shadduck | ............... | A61H 19/34 |

\* cited by examiner

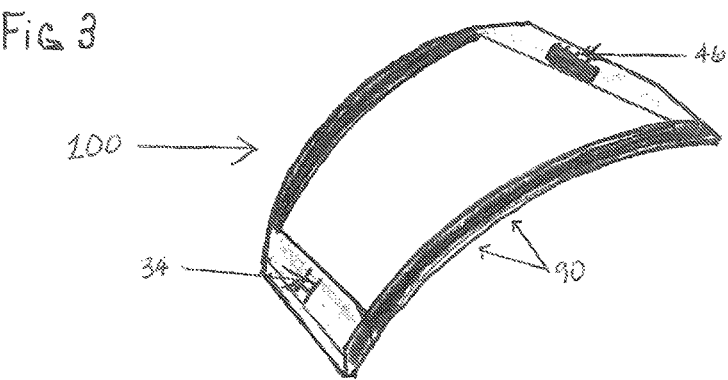
Fig 3
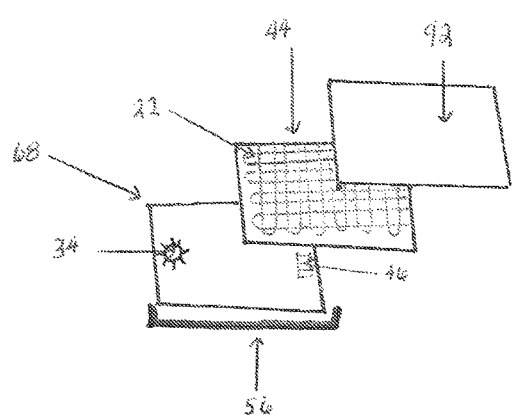
Fig 4
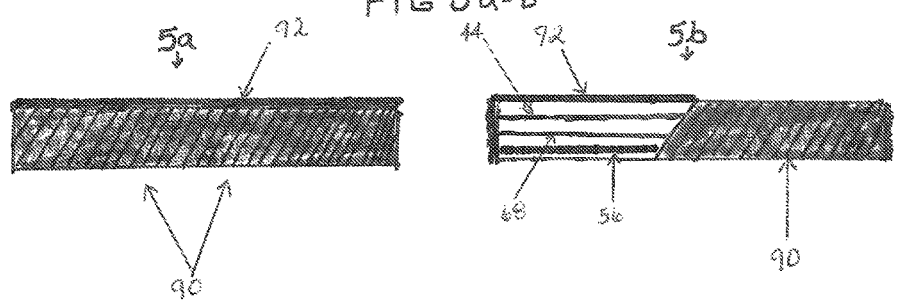
Fig 5a-b

SYSTEM OF COMMUNICATION IN A WEARABLE DEVICE

FIELD OF INVENTION

The present invention is directed to a system and method of distributing information and instructions for a wearable device, more specifically a system and method to dynamically transmit and/or receive information in real-time, and to be distributed to one wearable device, or is group of wearable devices configured to receive transmissions from a different apparatus, another wearable device, iPhone®, and/or a portable remote terminal.

PRIOR ART STATEMENT

Some sports allow coaches and/or individual players to provide game play information and instructions during the game, e.g. basketball, baseball, soccer, volleyball, paintball and football. Game play information may include but is not limited to the following: instructions, strategies, location, and or other instructions, in football, for example, the players are each required to learn all the "plays" in a playbook so that at game time a coach can selectively call plays with minimal instructions to be executed on the field. Prior art systems do not adequately address the problem of continual effective communication between coaches and/or individual, players throughout a game.

U.S. Patent application #20040102931, published May 27, 2004 by Ellis, describes a modular personal network (MPN) that includes multiple devices that may be worn, carried, or used in close proximity to a user. The devices communicate wirelessly. Functions of the MPN may be modified by adding or removing components. The MPN may communicate with a personal computer. General purpose devices may include a control unit, a display, a user input, and an audio output. The MPN may provide a variety of functions, including time, communication, entertainment, organization, guidance, athletic, medical, travel, outdoors, identity, security, and military.

U.S. Pat. No. 4,536,739, issued Aug. 20, 1985 to Nobuta, indicates an apparatus for communication of instructing information comprises a transmitter, a receiver and a data setting portion. A random access memory of the transmitter is in advance stored with a plurality of pieces of instructing data and any one of the pieces of instructing data, as stored, is read out and is displayed by a display. The receiver is provided with a random access memory for storing the instructing data as is similar to that of the transmitter. The corresponding instructing data is read from the random access memory as a function of the received address data and the instructing information is reproduced as a speech sound by means of a speech synthesizing circuit. The instructing data stored in the random access memory of the transmitter and the random access memory of the receiver is arbitrarily changed by means of the data setting portion.

U.S. Pat. No. 4,879,651, issued Nov. 7, 1989 to Little, claims a wrist carried microcomputer worn on an athletic wristband by a player for recording information based on a won-lost, outcome with a limited ability to track the type of a shot resulting in the outcome. The device is limited to single player and not usable in a team sport activity.

U.S. Pat. No. 6,330,961, issued Dec. 18, 2001 to Borja, provides an elongated pouch with various storage pockets for storage of personal articles therein, which is mounted upon a forearm of a user of the pouch such as the driver of an automobile. A personnel communicator device is positioned within the pouch, the personnel communicator device having a data transmission portion, typically a keyboard and a character display screen, facing the driver of the vehicle for facilitating data exchange between the driver and the personnel communicator device while operating the vehicle. The screen generated characters are displayed along a line parallel to the length of the forearm of the driver of the vehicle to facilitate easy reading of the characters by the driver of the vehicle.

U.S. Pat. No. 2,904,645, issued Sep. 15, 1959 to Saries, is for a football helmet containing a receiver, headphones, and other necessary components. The patent also provides for the installation of the device in various other types of helmets, such as construction helmets, and the like. No transmitting means is disclosed, however.

U.S. Pat. No. 5,142,700, issued Aug. 25, 1992 to Reed, shows a protective helmet, such as a football helmet, motorcycle helmet, construction helmet, or the like that comprises a shell made of impact-resistant material. Inside of the helmet is a complete transceiver system which allows two-way wireless communication between persons in the same location or to a remote base unit. No components of the system protrude, from either the interior or exterior of the helmet shell as the antenna follows the configuration of the shell centerline while one or more microphones are contained within elements of the face guard. A switch device, also contained within the face guard and including an illuminated element, is disposed within the field of view of the wearer.

U.S. Pat. No. 4,885,797, issued Dec. 5, 1989 to Leather, discloses a communication system for instructing individual members of a group and the group as a whole comprising a transmitter to be used by the instructor and a receiver for each member of the group which receiver contains an electric battery and is mounted on an elastically extensible article to be worn on the head of the respective member, each receiver designed to be extensible and to be contained within the extensible article, an input amplifier stabilized by a crystal oscillator and yielding an audio frequency signal, decoding means for sensing a sub-audible tone in that signal identifying that the signal is intended for the entire group or another sub-audible tone identifying that the signal is intended for the particular receiver, an output circuit for passing the signal to audio transducers, one over each ear of the member in use, when the decoding means yields a signal denoting that a sub-audible tone acceptable to that receiver is contained in the audio frequency signal, and in that the transmitter injects a sub-audible continuous tone under the control of the instructor to identify the member to be instructed onto the audio input to the receiver. An alternate embodiment shows the receiving unit in a sweat band for foot sports with the receiving unit being in one or two parts.

U.S. Patent Application #20050049080, published Mar. 3, 2005 by Hovington, provides a communication system for soccer coaches and their staff that enables them to provide training from a distance and in noisy environments to soccer players anywhere on the training field without interruption. Each player wears an elastic bellyband around the waist. The bellyband has a center pocket that houses a radio receiver that is connected to a custom ear mold.

U.S. Patent Application #20050170870, published Aug. 4, 2005 by Goldenberg, shows a communication system for use in sports training or during play, wherein a first user can communicate on a real time basis with at least one second user, wherein the system includes at least one digital transmitter module for readily facilitating transferring a verbal message from a first user to at least one second user, and at least one digital receiving module for readily facilitating the second user receiving the verbal message from the first user. Preferably, the transmitter is used by the first user, such as a trainer, for real time communication with at least one second user, such as a player during a game, via a receiving device worn by the player. Optionally, the system includes a multi-user activator for transmitting to more than one user.

U.S. Patent Application #20050212202, published Sep. 29, 2005 by Meyer, claims a telepath sports training system of communication for providing instruction, information, and verbal commands between a teacher and a student. An exemplary embodiment of the invention is particularly suited for use between a sports coach and the players on his or her team. The system of the present invention is preferably comprised of a microphone for the coach, a transmitter, at least one receiver, and at least one speaker for at least one player.

U.S. Pat. No. 5,600,730 is directed to a swimming training device that may be part of an overall training system. The device is deployable releasably in a swimming cap and can receive electromagnetic wave signals. The device can then convert the signals into electrical charges which are then translated into audible sound. The system includes the cap with the receiving device and a transmitting source. The transmitting source allows the broadcasting of verbal instructions, as well as music and timing signals.

U.S. Pat. No. 8,370,549 filed on Sep. 7, 2007 a USB device is used as part of an assembly having a carrier wherein the USB device is wearable. In addition, the USB device has a controller that communicates with a sensor to record and monitor athletic performance as an overall athletic performance monitoring system.

U.S. Ser. No. 12/286,476 Filed: Sep. 30, 2008 is directed to an apparatus for improving communications between players and coaches during a sporting event, more specifically allowing players to dynamically receive real-time communications from their coaches concerning intended game plays to be effected on the field or court. Said game apparatus comprises of a transparent, protective top cover having the same contour as a middle portion, and the display element are all enclosed by a rear cover forming a housing for a receiving means for receiving an encrypted signal of an intended game play from a portable remote terminal. The problem with this system is the reliability on the capacitive system with liquid crystal display ("LCD") or light emitting diode ("LED") type, plasma, touch screen or other types of displays that are deemed unreliable due to weather conditions and the rough nature of football during real time communications.

U.S. Ser. No. 13/017,184 Filed; Jan. 31, 2011 describes a system for delivering and using football plays includes a database with a number of football plays. A server is in communication with the database. The server includes a number of operating functions. A network is in communication with the server. A client is connected to the network. A printer is in communication with the client. The printer prints a playact from the football plays. A Wristband has a pocket for holding the playset. This system allows a coach to select plays and group them into a playset. The playsets are printed out and placed in a wristband. Since each play is numbered, the quarterback (or coach) can just call out the number of the selected play and each player can see what their assignment is.

U.S. Ser. No. 13/814,479 Filed Feb. 5, 2013 describes a wrist coach system (220) comprising a layout module and an output module. The layout module provides a user with menu features and navigational features. The menu features and the navigational features are configured to allow the user to create a play. The output module provides wrist coach instructions for the created plays. The Wrist coach instructions are configured to be viewed from a Wrist coach on the wrist of a player.

However, the afore-mentioned games have not been able to capitalize on technological advancements in the communications field as the method of communicating information still relies heavily on (a) verbal communications in a huddle; (b) running the plays over speakers; (c) hand signals; (d) a carefully scripted written play list on an armband, wristband, waistband or other wearable band; or (e) a transmitter in the players' helmet.

The problem with the foregoing methods of communications is that they each have their limitations in providing efficient and secure transmissions. For example, in football, calling the plays via speakers to transmitter in a helmet are generally not known for their reliability as on occasion, the transmission is garbled, interrupted, or the external noise level on the field is so high that the recipient may not be able to hear the play. As for hand signals that are transmitted either from the sidelines, on or off the field and/or court (collectively "the field"), both the hand signals and the resulting plays are heavily watched by the opposing team to anticipate and counter the play. This is especially true if a coach repeatedly uses the same hand signals to run certain plays. In that event, the opposing team may easily counter the play by calling its own plays, run interferences and/or intercept the ball.

Players and coaches alike are very aware of the foregoing limitations and some players, e.g. football players, have resorted to wearing an extra wide wristband, thighband or other types of wearable bands made of stretchable material with a Velcro® strap that unfolds to reveal a panel where the information and/or instructions are committed in writing for quick review. Except, in the heat of the game, the margin for error is still high as the player must unfold this wearable band and review several plays before identifying the intended game play, all within a matter of seconds. Thus, there is a need for a system and method of transmitting and receiving secure information and/or instructions in real-time during the game in a format that may be readily received, provides durability in rough field conditions and weather environments, and easily interpreted and universally understood by the players and or coaches.

This invention satisfies these long felt needs and solves the foregoing problems in an innovative and technologically savvy manner that the prior art has been unable to solve.

SUMMARY OF THE INVENTION

A wearable device (glove or wristband) that incorporates a system for delivering information and instructions such as football plays from a programmed application configured to display the information wirelessly transmitted from a separate portable electronic device.

In order to achieve the above-mentioned objective, the present invention uses a plastic flexible display. These flexible displays are cited as being "unbreakable", because they are made completely of plastic and do not contain glass.

Yet another object of the present invention is to provide a system and method that could detect an actual touch on a flexible plastic display for delivering information and instructions. This objective is accomplished using the HSS (heuristic signature sensing) technology.

Most touch sensitive devices, like those used in the iPhone and other computing devices, are known as capacitive systems. in the capacitive system, screens are made from multiple layers of glass. When you bring your finger up to the screen; the finger alters the electrical field, and measure a touch response. Environmental factors wreak havoc with capacitive systems: Temperature changes, liquid splashes, or wearing gloves can trigger a touch or keep a touch from triggering. A unique vernacular has sprung from this with phrases like "false-trigger" or "butt-dial." These issues have given rise to new industries like gloves that will work with touch screens.

Yet another object of the present invention is to provide a system and method that is designed and configured to overcome the problems the hinder the manufacturing process once a touch system is designed and configured and thresholds are set. In a capacitive environment, the humidity level of printed circuit boards can affect the dielectric constant of batches of boards differently, causing a touch system to feel different from pail to part or fail altogether. Adhesives are another culprit; adhering, potting, or optically bonding circuit boards is virtually never a perfectly uniform process, and changes in thickness, air gaps or bubbles can cause serious touch system challenges. Surface manipulation, such as grinding, milling, or painting, often yields variance. Conversely, due to the multiple layers of glass substrates on the front of a touch system display, the stiffness of the display would lead to possible malfunctions, durability and breakage issues in certain conditions such as football, soccer, etc., due to physical nature and demands of the game. Heuristic signature sensor technology solves the foregoing problems by measuring disruptions in an electric field. The process uses countermeasures that can be applied to overcome the limitations of thresholds. Removing thresholds from touch sensing unlocks the potential of the electric field, thereby boosting touch performance. Without using thresholds, sensors determine an actual touch event at the real touch surface rather than an arbitrary trigger point. These sensors signatures remain consistent, even if there is manufacturing variance that would make a touch event feel differently if it were driven by an arbitrary threshold.

Another object of the present invention is to provide protection and functionality in weather and water conditions. OLED (organic light-emitting diode) is the key panel technology used in the capacitive platform. OLED is a light-emitting diode (LED) in which the emissive electroluminescent layer is a film of organic compounds which emit light in response to an electric current created by the capacitive touch. Water can instantly damage the organic materials of the displays. HSS technology solves the foregoing problems by using a polyimide plastic tft backpane allowing sensors to remain functional when wet.

As used herein, illustratively, one embodiment, the wearable device is an athletic wristband being provided to at least one team player. In an alternate embodiment, the wearable device, is a sport specific glove. In either embodiment, the transceiver of the wearable device is configured for transmitting and/or receiving data signals containing game play instructions.

BRIEF DESCRIPTION OF THE DRAWING FIGURES

Further objectives and advantages of the present invention may be derived by referring to the detailed description and claims when considered in connection with the Figures.

FIG. 3 is a perspective view of the flexible display according to the above first embodiment, illustrating the bendable nature of the flexible display.

FIG. 4 illustrates an exploded top perspective view of a flexible display showing layered substrates.

FIGS. 5a & 5b illustrates diagrams for a frame housing the flexible display.

DETAILED DESCRIPTION OF PREFERRED EMBODIMENTS

While the embodiments are described herein being used within the game of football, the embodiments and devices described herein may be used within any suitable sporting event, athletic event, and/or any other event. In the description, references are made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

Illustrated in FIGS. 1-8, is a wearable device that is configured to send and receive information such as game play instructions from a computer or a portable remote terminal. The computer or remote terminal may have a processor and a memory on which processor-executable instructions are tangibly embodied. The computer or remote terminal, can have a programmed application, from which information and game play instruction may be inputted via a user interface and communicated wirelessly to the wearable device. Moreover, in certain embodiments, the programmed application can be configured with pre-stored data ready to be encrypted by a signal containing a game play instruction intended for execution on a field during a game. The game play instruction includes but is not limited game instructions, game strategies, specific plays, location information, and any other allowable game play instructions chosen by a skilled artisan. The game play instruction may be transmitted to a specific wearable device, or all wearable devices provided to teammates. The computer or portable remote terminal may include a digital audio converter, used to convert the encrypted and/or decrypted signal containing the game play instruction in digital data format. The wearable device may be used in a variety of sports, for example, football, baseball, volleyball, soccer, paintball and basketball.

Figure 1:
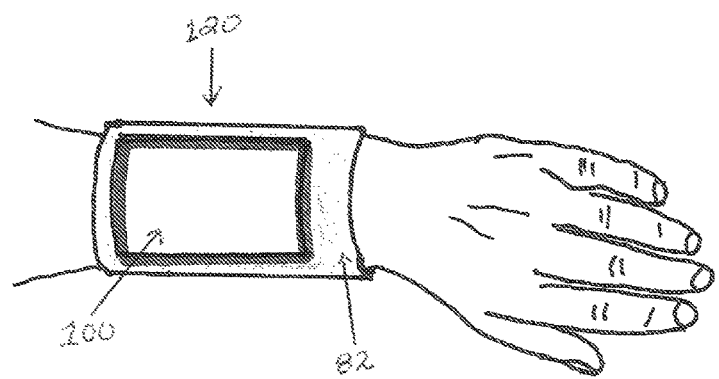
FIG. 1 is an illustrative view of a wristband having a flexible display according to an embodiment of the present invention.
Figure 2:
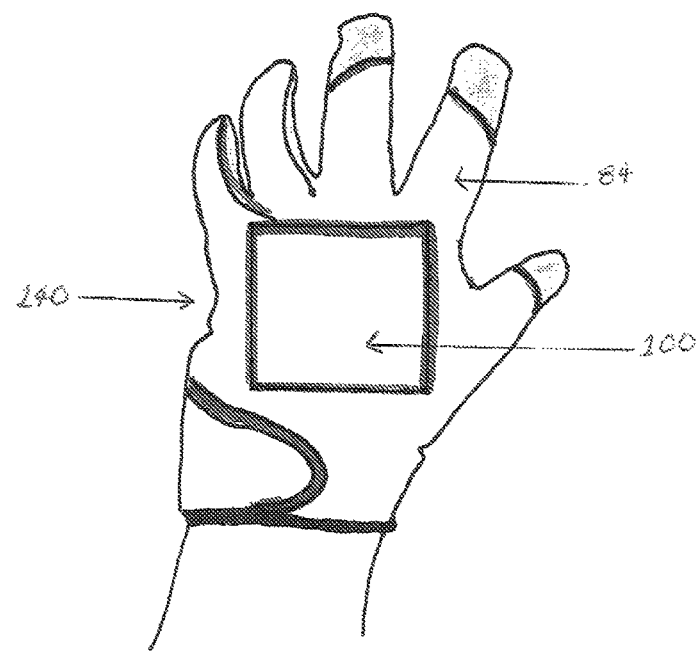
FIG. 2 is an illustrative view of sport specific glove having a flexible display according to an embodiment of the present invention.

In FIGS. 1 and 2, a wearable device described as flex signature wristband 120 and flex glove 140 that incorporates a system for delivering and receiving information into a small plastic flexible display 100 used by a player 70 receiving information on a wristband 82 and or glove 84 viewed on a screen 60.

In certain embodiments, the wearable device is attached to a flexible material that is configured to secure the wearable device to the user. Additionally, the wearable device can be formed from a semi-rigid material for preventing breakage, damage and injury to the wearer. The wearable device can be capable of absorbing shock from the impact associated with certain sports. Additionally, the wearable device may include programmable buttons positioned for touch screen operation that are able to control the display of the received game play instruction, providing feedback to the sender of the game play instruction or configured for transmitting the player's current information to other players within the group.

In FIG. 1, is a flex signature wristband 120 comprising a flexible plastic display 100 webbed into a wristband 82 as worn by a player participating in a sporting event on a playing field. The wristband encircles the wrist and forearm area of an arm of the player, a means of securing the band to the player using hook and loop fasteners or other tape to the wrist and forearm, were the wristband 82 is configured for receipt of digital transmissions from a coach 50 or another player. The flexible plastic display 100 comprising a menu for a player to review and send information on the viewing screen.

In FIG. 2, illustrates a view of a flex-glove 140 comprising a flexible plastic display 100 webbed into an athletic glove 82 as is worn by a player, such as a pass receiving player, an offensive player, or a defensive player on a football playing field. The flex glove is designed to provide both the required protection and flexibility to the hands of a football player. For instance, an offensive lineman's glove has a hand-protecting portion with finger and thumb pads, which cover at least the first phalange of the fingers and thumb.

This reduces the exposure of the fingers and thumb to damage and at the same time, allows adequate exposure for using the hands in either dealing with an opponent or grasping a free ball. Wide receiver gloves are shaped to fit tight and flexible encircling the whole hand.

FIG. 3, illustrates an exemplary flexible plastic display 100 to enable two-way communication as described herein. More specifically, in the exemplary embodiment, the flexible display 100 is described as being used in a football game, Moreover, in the exemplary embodiment, flexible plastic display 100 includes hook-and-loop fastener webbing tape 90. The hook-and-loop fastener webbing tape 90 enables the flexible plastic display 100 to be coupled to a desired wearable device, such as on a wristband 82 of a quarterback 70, or on an athletic glove 84, such as on a wide-receiver, lineman or defensive player.

The flexible plastic display 100 can be configured for viewing a received decrypted signal containing game play instruction intended for execution on the field during the game. In certain embodiments, the flexible plastic display 100 is enclosed around a thin rubber like frame, which is webbed into the wearable device fabric using strong durable threads.

Additionally, a flexible bending sensor 68 uses resistors to adjust the sensitivity of the touch signature sensors 22 which allows an actual touch to be detected on the flexible plastic display 100 of the wearable device, which is designed to operate accurately and reliably in harsh environments.

In the exemplary embodiment, flexible plastic display 100 includes a micro processing unit (MPU) 46, an integrated display driver chip 34, a converter, a memory, a user interface, and at least one power source (not shown), such as one or more batteries or solar power, that provides power to the components contained within flexible plastic display 100. In the exemplary embodiment, the flexible plastic display 100 is also impact-resistant to facilitate protecting the internal components during high impact events.

In a specific embodiment, the flexible bending sensor 68 has a plurality of resistors that change value based on how much the resistors flex. If the resistors unflexed, the resistance is roughly 10 KO. When the resistors in the flexible bending sensor 68 are flexed to the maximum, the resistance rises to about 20 KO. Additionally, the flexible bending sensor 68 can use an analog input on a microcontroller (with a pullup resistor) or a digital input with the use of a 0.1 uF capacitor for RC timing that could detect both convex and concave bending.

FIG. 4 is an exemplary overview diagram of an embodiment of the present invention showing flexible layers of substrates coated with a thin film/layer of transparent (TFT) conductive material that conducts a continuous electrical current across the plastic touchscreen sensor. Accordingly, flexible may include a substrate such as a sheet of polyethylene terephthalate (PET). In lieu of PET, substrates may be a flexible sheet of another suitable material, e.g., polycarbonate polyester, polyvinyl chloride, polyether sulfone, polyimide polyether imide, cellulose triacetate and polyethylene naphthalate. Onto the substrates are applied the materials fundamental to integrated circuits: such as an insulator (silicon dioxide), semiconductor (crystallized silicon or polysilicon), dopants of selected elements, metal connectors, or any other sufficient material.

This illustrative view is merely one embodiment and example embodiments are not limited thereto, e.g., sensing patterns, touch screen matters, and substrates. In this illustration, the protective lens 92 is polarized using a flexible, conductive polyimide plastic that protects the display device. An electrode substrate 44 is sandwiched between the two polarization films. The electrode substrate 44 incorporates a touch signature sensor 22 designed to capture and use information from the electric field of the protective lens 92. The touch signature sensors 22 are configured to send raw signal data to the integrated display driver chip 34 to processes the raw data. The integrated display driver chip 34 with a sensing controller includes a transparent or translucent substrate that allows light to pass therethrough, that has electrically conductive traces established thereat. The sensing controller circuitry acquires the data from touch signature sensors 22 which may include the coordinates of each sensor and the pressure exerted on each sensor. In another embodiment, the sensor is configured to process the raw data itself. The sensing controller receives the pulses from the sensor and turns them into data understood by the microprocessing unit (MPU) 46. The sensing controller may perform filtering and/or conversion processes. Filtering processes are typically implemented to reduce congestion of data stream so that the (MPU) 46 will not overload with redundant or nonessential data. The conversion processes may be implemented to adjust the raw data before sending or reporting them to the (MPU) 46. A bending sensor 68 interfaces between the (MPU) 46 and an AD converter. The bending sensor 68 is underneath the electrode substrate 44, and can be augmented so that it could detect both convex and concave bending as the bending sensor 68 is attached to a flexible backlight unit 56. The flexible backlight unit 56 consists of a thin light-guide plate (0.4 mm in thickness), 24 LED chips, and optical films including reflection, diffusion, and prism sheets.

FIG. 5a is an enlarged perspective view of the top of the protective lens 92 embedded in hook-and-loop fastener webbing tape 90 used to bound a flexible plastic display to a wearable device such as wristband 82 or glove 84

FIG. 5*b* is an enlarged perspective view of substrates housed inside of hook-and-loop fastener webbing tape 90. The cross section illustrates a layer of substrates including the top lens 92, electrode substrate 44, bending sensor 68, and backlight unit 24. Each substrate has such as a coating or layer of transparent conductive overcoat (TCO) such as indium tin oxide (ITO) or the like disposed on a surface thereof, and with a metallic layer or coating (such as an opaque or partially opaque or partially transparent metallic layer or coating, such as, for example, a copper layer or coating, a chromium layer or coating, a niobium layer or coating, a neodymium layer or coating, a silver layer or coating, a molybdenum layer or coating, and/or a layer or coating of alloys of these metals).

Figure 6:
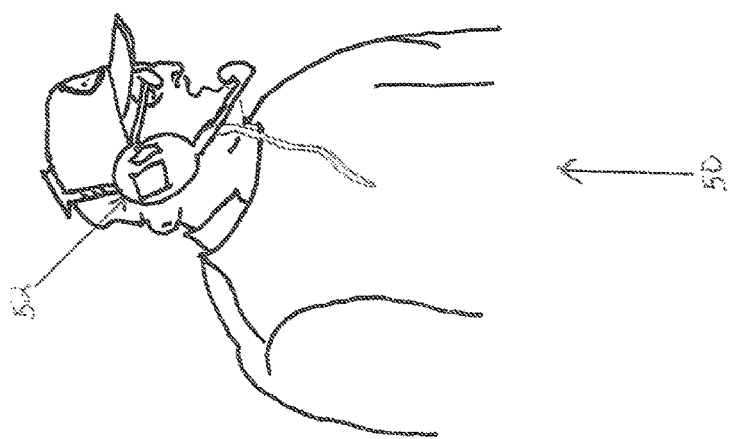
FIG. 6 is a perspective side view of a football coach transmitting information.

FIG. 6 is a perspective view of a coach 50 (football) is a perspective side view as a football game progresses a coach located on the field, speaks into a headset 52, or other means to transmit a signal to the quarterback 70 to execute a particular intended game play instruction.

Figure 7:
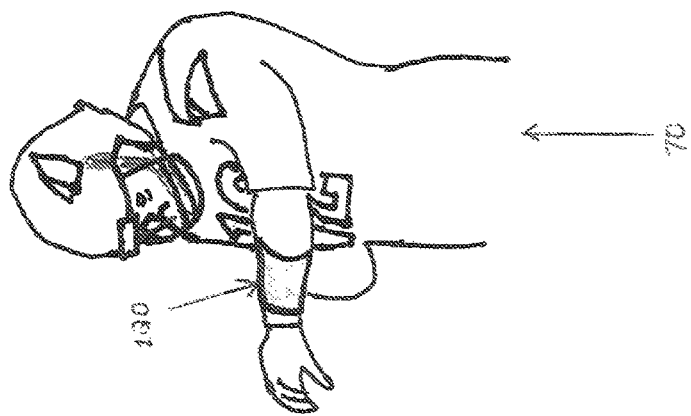
FIG. 7 is a perspective view of a football player (quarterback) with a view of wristband.

FIG. 7 is a perspective view of a flex signature wristband 120 worn by a football player 70, such as a quarterback on the field in a football game viewing the screen indicating a particular play to be executed in the game.

Figure 8:
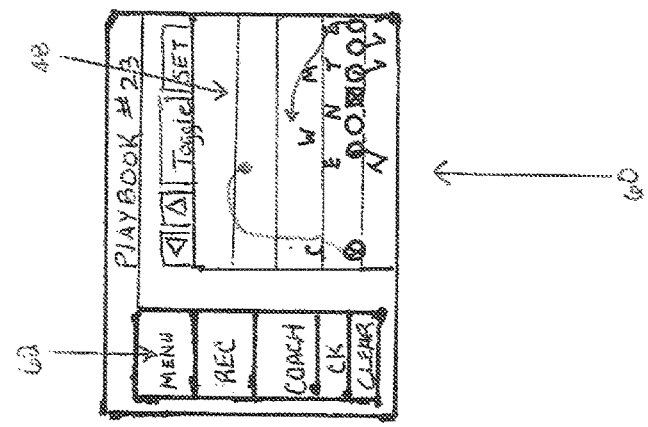
FIG. 8 is a perspective side view of a display screen of the present invention.

FIG. 8 is an illustrated view of the panel screen 60 represents a curved, convex and concave swine. The panel display screen 60 includes all relevant information and game play instruction in separate, preferably touch-sensitive buttons, a menu button 62 is used to toggle and review programmed plays: such as passing plays, running plays, and individual plays. The menus 62 can be used to select and send previously installed plays and instructions and currently input instructions to other players to use on the playing field. Additionally, the panel screen will include a view area 48 wherein said received game play instruction may comprise of any one or more of the following formats: text, visual, sketch and audio.

What is claimed is:

1. A wearable device comprising:
    a main body having a heuristic signature sensing flexible display, a sensing controller, a digital audio converter, and a micro-processing unit, wherein the digital audio converter is configured to convert a signal into a digital format, the flexible plastic display having a touch signature sensor, an electrode substrate, a bending sensor, and a protective lens, the sensing controller configured to interpret pulses from the plastic touch signature sensor into data understood by the micro-processing unit, the flexible bending sensor is configured to alter the electronic resistance in the electrode substrate based on bend of the plastic display, the main body formed of a shock absorbing material, and the micro-processing unit in communication with the digital audio converter, and the micro-processing unit configured to transmit and receive information including a game play; and
    a transparent conductive overcoat covering each of the touch signature sensor, the electrode substrate, the bending sensor, and the protective lens,
    wherein the wearable device is a glove.

2. The wearable device of claim 1, wherein the transparent conductive overcoat includes one of indium tin oxide, copper, chromium, niobium, neodymium, silver, and molybdenum.

3. The wearable device of claim 1, wherein the flexible backlight unit has a thin guide plate, 24 LED chips, and optical films.

4. The wearable device of claim 1, wherein the plastic touch signature sensor is made of polyimide.

5. A method of sending game plays to a wearable device, comprising:
    providing a main body having a heuristic signature sensing flexible display, a sensing controller, a digital audio converter, and a micro-processing unit, wherein the digital audio converter is configured to convert a signal into a digital format, the flexible plastic display having a touch signature sensor, an electrode substrate, a bending sensor, and a protective lens, the sensing controller configured to interpret pulses from the plastic touch signature sensor into data understood by the micro-processing unit, the flexible bending sensor is configured to alter the electronic resistance in the electrode substrate based on bend of the plastic display, the main body formed of a shock absorbing material, and the micro-processing unit in communication with the digital audio converter, and the micro-processing unit configured to transmit and receive information including a game play, and a transparent conductive overcoat covering each of the touch signature sensor, the electrode substrate, the bending sensor, and the protective lens, wherein the wearable device is a glove;
    providing a computer with a processor and a memory on which processor-executable instructions are tangibly embodied, the computer configured to transmit and receive information; and
    transmitting the information, by the computer, to the wearable device.

\* \* \* \* \*